(12) United States Patent
Wagner et al.

(10) Patent No.: US 6,717,665 B2
(45) Date of Patent: Apr. 6, 2004

(54) POLARIMETER

(75) Inventors: Jeff A. Wagner, Washington Twp., NJ (US); Thomas G. Bancroft, Byram Twp., NJ (US)

(73) Assignee: Rudolph Research Analytical, Flanders, NJ (US)

( * ) Notice: Subject to any disclaimer, the term of this patent is extended or adjusted under 35 U.S.C. 154(b) by 83 days.

(21) Appl. No.: 10/097,189

(22) Filed: Mar. 13, 2002

(65) Prior Publication Data

US 2003/0174323 A1 Sep. 18, 2003

(51) Int. Cl.$^7$ .............................................. G01N 21/01
(52) U.S. Cl. ..................... 356/244; 356/367; 250/461 R
(58) Field of Search ................................ 356/244, 246, 356/369–370, 39–41; 250/343, 461 R, 458

(56) References Cited

U.S. PATENT DOCUMENTS

| | | | | |
|---|---|---|---|---|
| 3,695,772 A | * | 10/1972 | Spyropoulos | 356/246 |
| 4,180,739 A | * | 12/1979 | Abu-Shumays | 250/461.1 |
| 4,467,204 A | * | 8/1984 | Kysilka et al. | 250/343 |
| 4,749,276 A | * | 6/1988 | Bragg et al. | 356/246 |
| 5,857,341 A | * | 1/1999 | Amakusa | 62/51.1 |
| 6,046,804 A | * | 4/2000 | Kawamura et al. | 356/244 |

FOREIGN PATENT DOCUMENTS

DE     100 56 131     * 11/1999

* cited by examiner

*Primary Examiner*—Frank G. Font
*Assistant Examiner*—Sang H. Nguyen
(74) *Attorney, Agent, or Firm*—Kaplan & Gilman, LLP

(57) ABSTRACT

A sample cell in a polarimeter comprises a thermally conductive body enclosing a substantially cylindrical internal volume with an insulating outer cover which leaves one face exposed for complementarily contacting a temperature controlled base plate so as to keep the sample cell at a predetermined temperature, and a means for positioning the sample cell at a predetermined position such that a measuring light beam longitudinally passes through the sample cell. The water jacket system required for the conventional cylindrical sample cells is eliminated. A cell holder for holding a cylindrical sample cell in a polarimeter comprises a heat transfer element having a concave cylindrical heat transfer surface for complementarily contacting an external cylindrical surface of the cylindrical sample cell so as to keep the sample cell at a predetermined temperature. The heat transfer element is thermally conductive to a thermal electrical conductor element the temperature of which is controllable by an electric current. The cylindrical sample cell is positioned in the light path of the polarized light beam by a cell mount formed by the heat transfer element, or by a pair of flanges resting on a pair of parallel rails. The invention eliminates the use of the water jacket temperature control system for the cylindrical sample cells.

55 Claims, 9 Drawing Sheets

POLARIMETER

FIELD OF THE INVENTION

The present invention relates to polarimeters, and more particularly, to a sample cell and sample cell holder in which a thermo electric cooler is used to control the temperature of the sample cell and the liquid contained therein.

BACKGROUND OF THE INVENTION

A polarimeter is an instrument for measuring the optical activity exhibited by an optically active substance including inorganic and organic compounds. In particular, the plane of polarization of a linearly polarized light beam is rotated when passing through the optically active substance, and the rotation is determined by the specific substance, the concentration of that substance and the optical pathlength of the light through the substance contained in the sample cell, whereby the concentration of the specific substance can be calculated by the measured rotation. The optical rotation is also affected by the temperature of the substance contained in the sample cell, and thus it is desirable, and in many cases required by governing regulations, that the temperature of the sample substance be controlled to be at a set point for precise measurement.

As shown in FIG. 1(A) and (B), a sample cell 11 is usually a cylindrical tube so as to minimize the amount of the sample substance that is in the cell but not in the light path, referred to as "dead volume". A pair of flanges 15 are provided at opposite ends of the sample cell 11, each with a beam aperture 18 therein for allowing the polarized light beam (shown as arrow 17) to pass therethrough. The flanges are usually standard in size for properly positioning the sample cell 11 in the light path when the pair of flanges sit on the cell holder constituted by a pair of parallel rails 16. The flanges may be removable from the sample cell 11 to facilitate cleaning of the cell. The temperature control of the sample substance is realized by circulating water in a water jacket 14 around the external surface of the sample cell 11 containing the sample substance 12. The water jacket 14 is formed by an outer tube 13 communicated with a water tube 19 connected to a water source at a predetermined temperature. However, such a water temperature control system is complicated in structure, comprising a water jacket and cooling tubes. Furthermore, it is inconvenient to connect and disconnect the tubing when cleaning the cell and changing the sample. It also takes long time to change the temperature set point.

Recently, thermoelectric temperature control techniques such as thermo electric coolers (TEC) have been introduced for temperature control in a polarimeter. The temperature of one side of a TEC device, which is usually a flat plate in shape, is controllable by an electric current. Heat can be made to flow through the device in either direction as required. As shown in FIG. 2, a TEC element 63 with a heat sink 64 is provided to be thermally conductive with a rectangular cell holder 62 accommodating a rectangular sample cell 61. A polarized light beam (shown as arrow 67) passes through the sample cell 11 via the apertures 68 provided on the cell holder 12. The solid TEC element 63 eliminates the complication and inconvenience of the water tubing required in the conventional cylindrical cell samples. Furthermore, the temperature of the cell holder 62 and therefore the sample cell 61 can be easily and quickly controlled at a set point. However, the rectangular sample cell 61 assumes a high dead volume and requires a larger sample volume to fill. This is costly when the measured substance is precious. The other problem with such a rectangular structural design is that the cell holder 62 can not work with conventional standard cylindrical sample cells which are commonly used in the industry. In addition this design was not able to control temperature within the limits required by relevant governing regulations.

SUMMARY OF THE INVENTION

An object of the invention is to provide a sample cell with a substantially cylindrical internal volume with its temperature controllable by a TEC element.

A further object of the invention is to provide a cell holder which is capable of holding both the inventive sample cell in a temperature controlled mode and conventional standard cells which are not temperature controlled by the cell holder. These conventional cells my be either of the water jacketed temperature controlled type or the non jacketed, non temperature controlled type.

A further object of the invention is to provide a cell holder for holding cylindrical sample cells with its temperature controllable by a TEC element.

A further object of the invention is to provide a cell holder with TEC temperature control unit which is capable to work with the conventional standard sample cells currently in common use.

To achieve the above objects, the sample cell of the present invention comprises a thermally conductive body enclosing a substantially cylindrical internal volume with an insulating outer cover which leaves one face exposed for complementarily contacting a temperature controlled baseplate so as to keep the sample cell at a predetermined temperature, and a means for positioning the sample cell at a predetermined position such that a measuring light beam longitudinally passes through the sample cell.

Thus, the temperature of the sample cell, which is less in dead volume, is controlled by the temperature control means. The water jacket system required for the conventional cylindrical sample cells is eliminated.

Preferably, the base plate which is fixedly positioned relative to the light path of the light beam for positioning purposes, is temperature controlled by means of being thermally conductive with a TEC element.

In a preferred embodiment, the heat transfer element is a cell mount on which the cylindrical sample cell rests. The cell mount is placed on the base plate in a predetermined position.

Preferably, the base plate comprises a slant upper surface on which the cell mount rests, and the cell holder further comprises a horizontal rail. The rail, on the one hand, stops the cell mount at a predetermined position on the base plate, and on the other hand, enables the inventive cell holder capable of supporting a conventional standard cylindrical sample cell by supporting its flanges directly resting on the rail and the slant upper surface of the base plate.

In another preferred embodiment, the heat transfer element is a cover resting on the cylindrical sample cell which sits on a pair of parallel rails. Preferably, the heat transfer element is detachably connected to the base plate so that the base plate can work with different heat transfer elements for different sizes of cylindrical sample cells.

BRIEF DESCRIPTION OF THE DRAWINGS

The above and other advantages and features of the present invention will be clearer from the following detailed description of the preferred embodiment of the present invention with reference to the accompanying drawings, in which.

DETAILED DESCRIPTION OF THE INVENTION

The invention is now described in detail with reference to the preferred embodiments shown in FIGS. 3–9 in which the same numerals are used for designating similar elements.

Figure 3A:
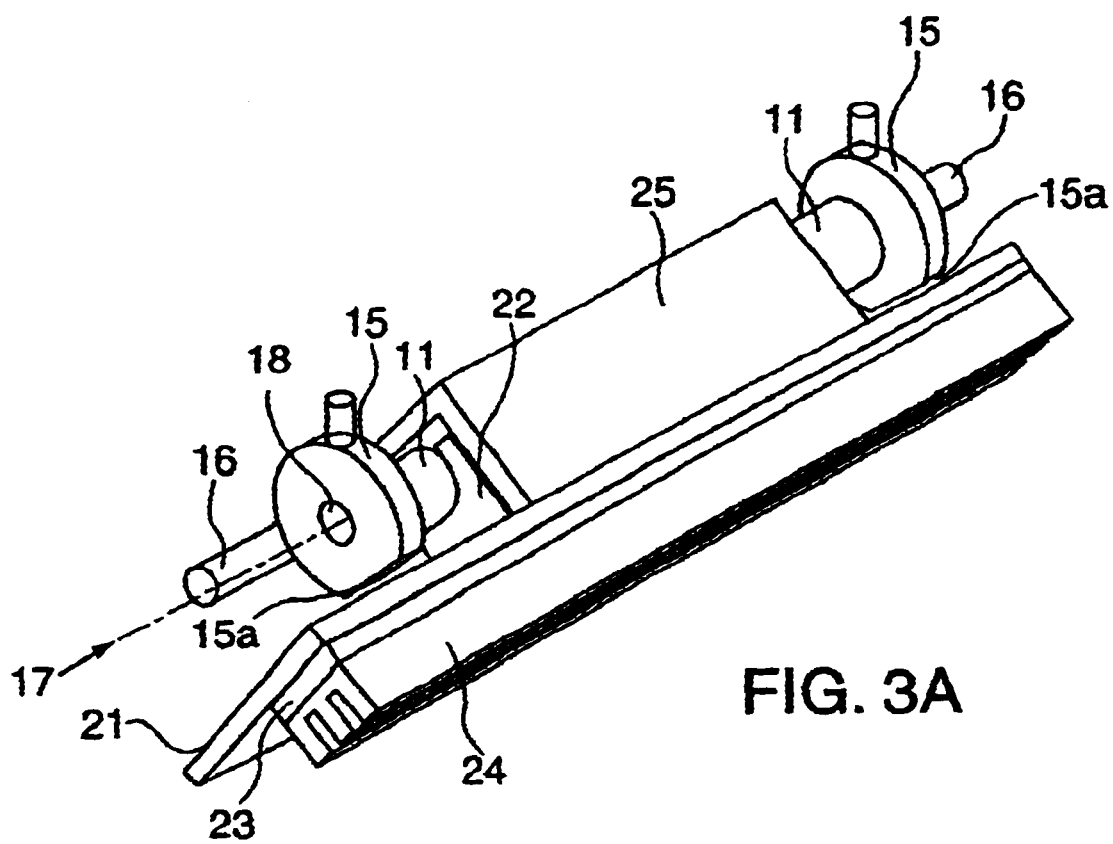
FIGS. 3(A) and 3(B) are perspective and sectional views respectively of a first embodiment of the cell holder according to the present invention.
Figure 3B:
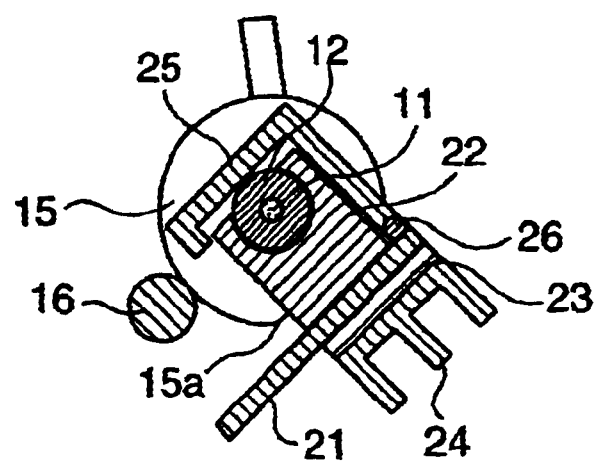

A cell holder according to the first embodiment of the present invention is illustrated in FIGS. 3(A) and 3(B). The cell holder comprises a cell mount 22 having a concave cylindrical surface for complementarily accommodating a cylindrical sample cell 11 therein. The cell mount 22 rests on a base plate 21 under which a thermal electric conductor (TEC) element 23 is attached. Both the cell mount 22 and the base plate 21 are made of thermally conductive materials so that the temperature of the cell mount 22 and therefore its concave cylindrical surface is controlled by the TEC element 23. With the concave cylindrical surface of the cell mount 22 as a heat transfer surface, the sample cell 11 is thermally conductive with the TEC element 23, whereby its temperature is kept the same as the TEC element 23 which is controlled at a set point by an electric current. TEC element 23 is provided with heat sink 24 comprising plurality of cooling fins.

The base plate 21 is fixedly secured in its position relative to the light path of the measuring polarized light beam (shown as arrow 17) for the purpose of the positioning of the sample cell 11 supported by the cell mount 22. As shown in FIGS. 3(A) and 3(B), the base plate 21 assumes a tilted posture such that its upper surface is slanted. A single horizontal rail 16 is provided parallel to the slant upper surface of the base plate 21, also for the positioning of the sample cell 11, which will be described in detail below.

The sample cell 11 is provided with a pair of circular flanges 15 each with a central aperture 18 for the light beam 17 to pass through the sample substance 12 contained in the sample cell 11. The flanges 15 abut on the rail 16, whereby the cell mount 22 is stopped at a predetermined position from further movement along the slant upper surface of the base plate 21. It is noted that the flanges 15 are partly removed at 15a so that they will not touch the slant upper surface of the base plate 21. Thus, the positioning of the sample cell 11 is realized by the contact between the flanges 15 and the rail 16 as well as by the contact between the cell mount 22 and the slant upper surface of the base plate 21.

An enclosing member 25 is provided to form, together with the concave cylindrical surface of the cell mount 22, a longitudinally complete enclosure for the sample cell 11. The enclosing member 25 may be attached to the cell mount 22, e.g., by a hinge connection 26. The enclosing member 25 is made of a thermally insulating material for preventing the sample cell 11 from exposure to ambient environment.

Alternatively, the enclosing member 25 may be made of a thermally conductive material for enhancing the heat transfer between the cell mount 22 and the sample cell 11. Preferably, a concave surface may be formed in the internal surface of the enclosing member 25 to complimentarily covering on the sample cell 11.

Figure 4A:
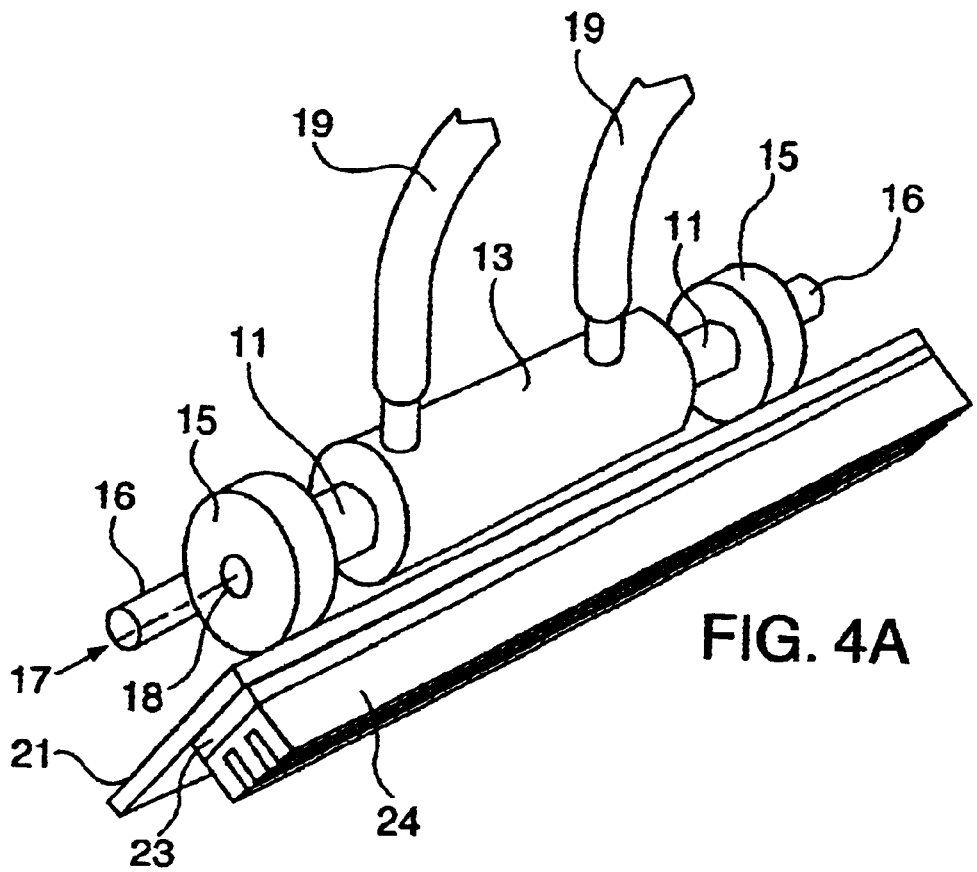
FIGS. 4(A) and 4(B) are perspective and sectional views respectively of the first embodiment in FIGS. 3(A) and 3(B) when used with a conventional standard cylindrical sample cell.
Figure 4B:
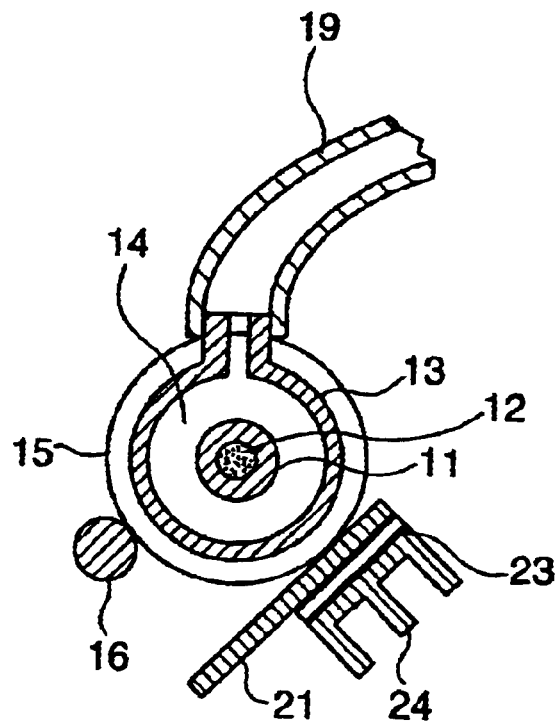

One important advantage of the cell holder in FIGS. 3(A) and 3(B) is that it is also capable of working with the conventional standard cylindrical sample cells with or without a water temperature control system. As shown in FIGS. 4(A) and 4(B), the pair of flanges 15 of a conventional standard cylindrical sample cell 11 can directly sit on the single rail 16 and the slant upper surface of the base plate 21. The positioning of the sample cell 11 is realized by the contact between the flanges 15 and the rail 16 as well as by the contact between the flanges 15 and the slant upper surface of the base plate 21.

Thus, the cell holder shown in FIGS. 3(A) and 3(B) can work with both the conventional standard cylindrical sample cells with water jacket temperature control system that are currently vastly used in the industry, and the novel cylindrical sample cell 11 with its flanges partly removed as shown in FIGS. 3(A) and 3(B).

Figure 5A:
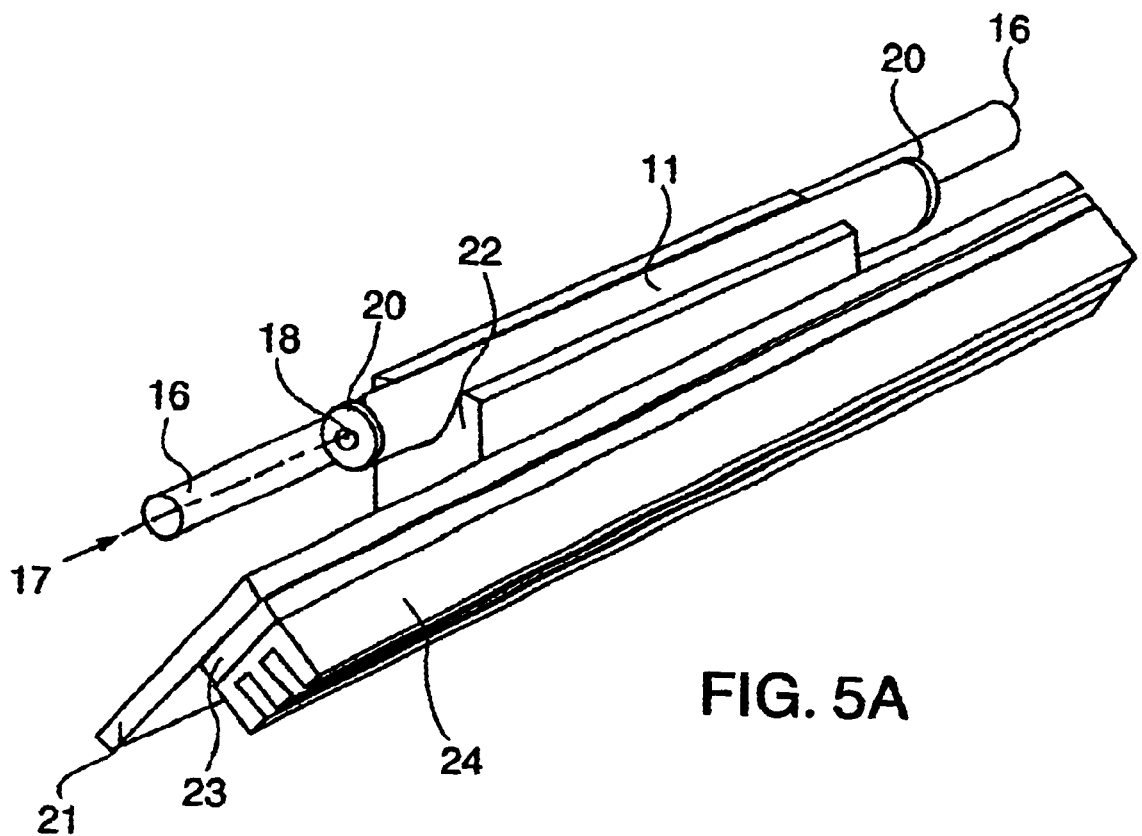
FIGS. 5(A) and 5(B) are perspective and sectional views respectively of a second embodiment of the cell holder according to the present invention.
Figure 5B:
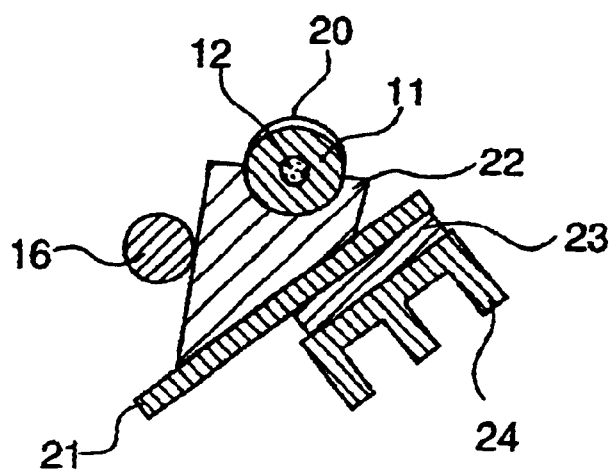

Another embodiment of the cell holder is shown in FIGS. 5(A) and 5(B), in which the rail 16 directly abuts against a side surface of the cell mount 22 to stop it at a predetermined position on the slant upper surface of the base plate 21. The cylindrical sample cell 11 in this embodiment does not need the flanges, thus substantially decreasing the cost of manufacture. The positioning of the sample cell 11 is also improved as there is no force applying to the sample cell from the flanges as in the case shown in FIGS. 3(A) and 3(B).

In this embodiment, the upper surface of the cell mount 22 on which the concave cylindrical surface is provided is generally horizontal so as to stably support the sample cell 11 thereon. A pair of caps 20 with light beam apertures 18 are provided at its opposite ends for facilitating the cleaning of the sample cell. The cell holder in this embodiment is also capable to work with conventional standard cylindrical sample cells as shown in FIGS. 4(A) and 4(B).

Temperature sensors may be used via insertion in the sample cell and/or permanently embedding such sensors in the base plate in accordance with known techniques. Such techniques, and others, are known in the art and not described in detail herein.

Figure 6A:
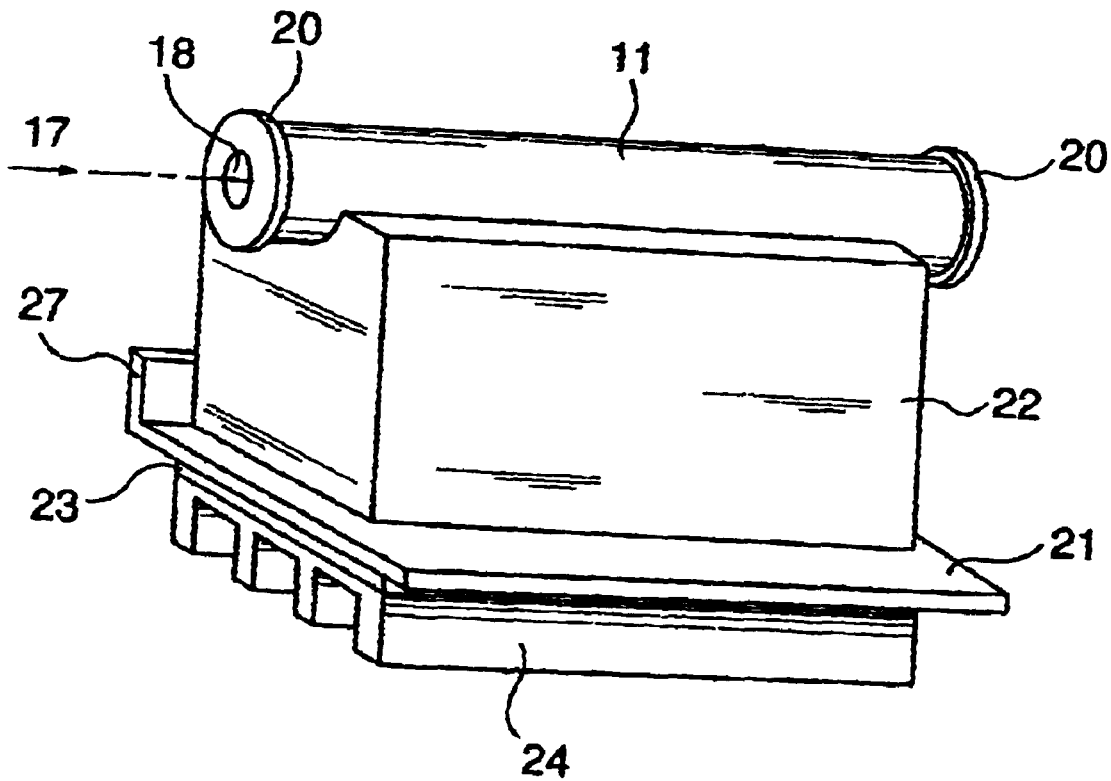
FIGS. 6(A) and 6(B) are perspective and sectional views respectively of a third embodiment of the cell holder according to the present invention.
Figure 6B:
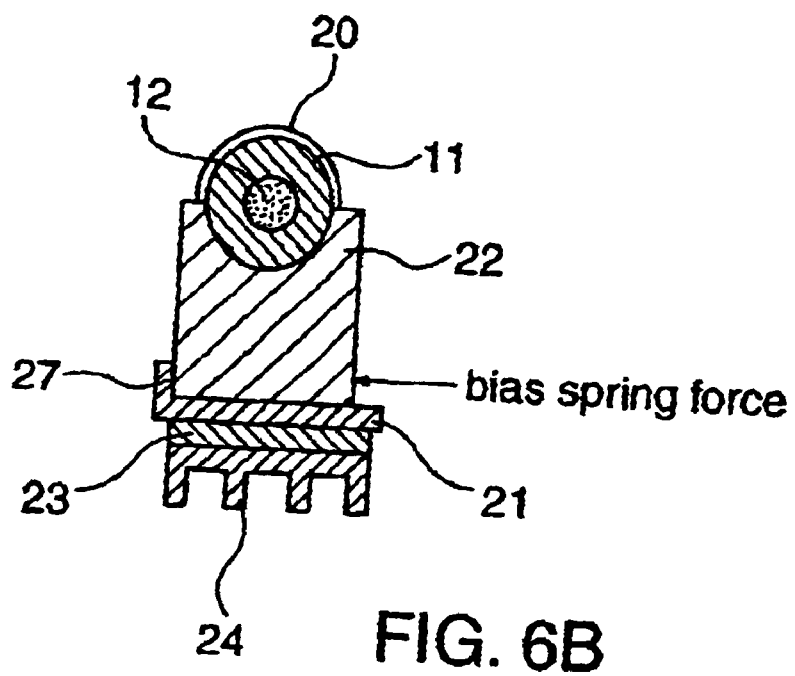

FIGS. 6(A) and 6(B) illustrate a cell holder according to a third embodiment of the present invention, in which the base plate 21 is horizontally positioned, thus eliminating the need of the rail 16 in FIGS. 3–5. The cell mount 22, which supports the cylindrical sample cell 11 in its concave cylindrical heat transfer surface, rests on the horizontal upper surface of the base plate 21. Same as in the embodiments in FIGS. 3–5, the base plate 21 is fixedly secured in position relative to the light path for the purpose of the positioning of the cell mount 22 and therefore of the sample cell 11. To prevent the lateral movement of the cell mount 22, a stopper 27, which may be in the form of a side wall, is provided on the upper surface of the base plate 21 to stop the cell mount 22. A bias spring force may also be provided to ensure the cell mount 21 abut against the stopper 27 (see FIG. 6(B)).

Figure 7A:
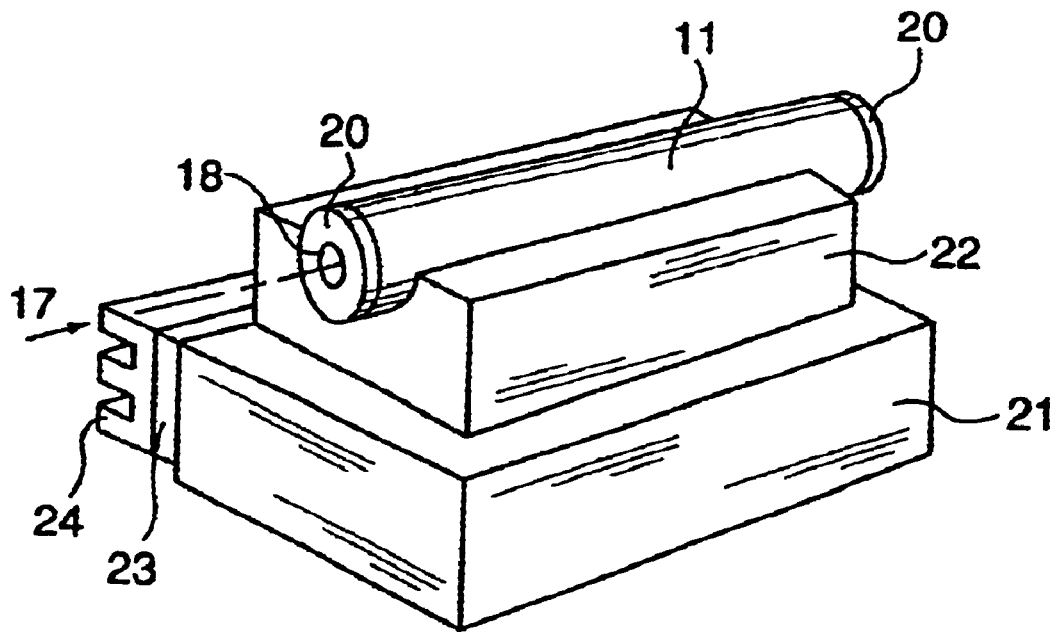
FIGS. 7(A) and 7(B) are perspective and sectional views respectively of a fourth embodiment of the cell holder according to the present invention.
Figure 7B:
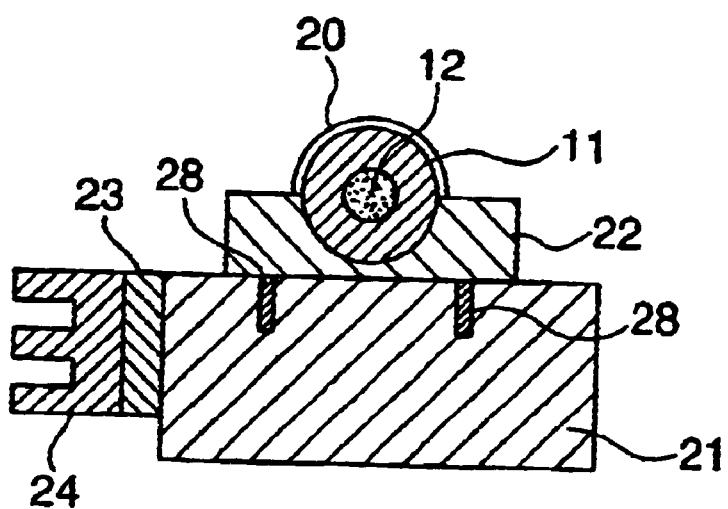

FIGS. 7(A) and 7(B) illustrate a cell holder according to a fourth embodiment of the present invention, which is similar to that shown in FIGS. 6(A) and (B), and thus only the different features are described here. In this embodiment, the positioning of the cell mount 22 on the base plate 21 is realized by multiple positioning pin-hole connections 28 (two of them are shown in FIG. 7(B)) instead of the stopper 27. It is also noted that the TEC element 23 is shown to be attached to the side wall of the base plate 21 in this embodiment.

Figure 8A:
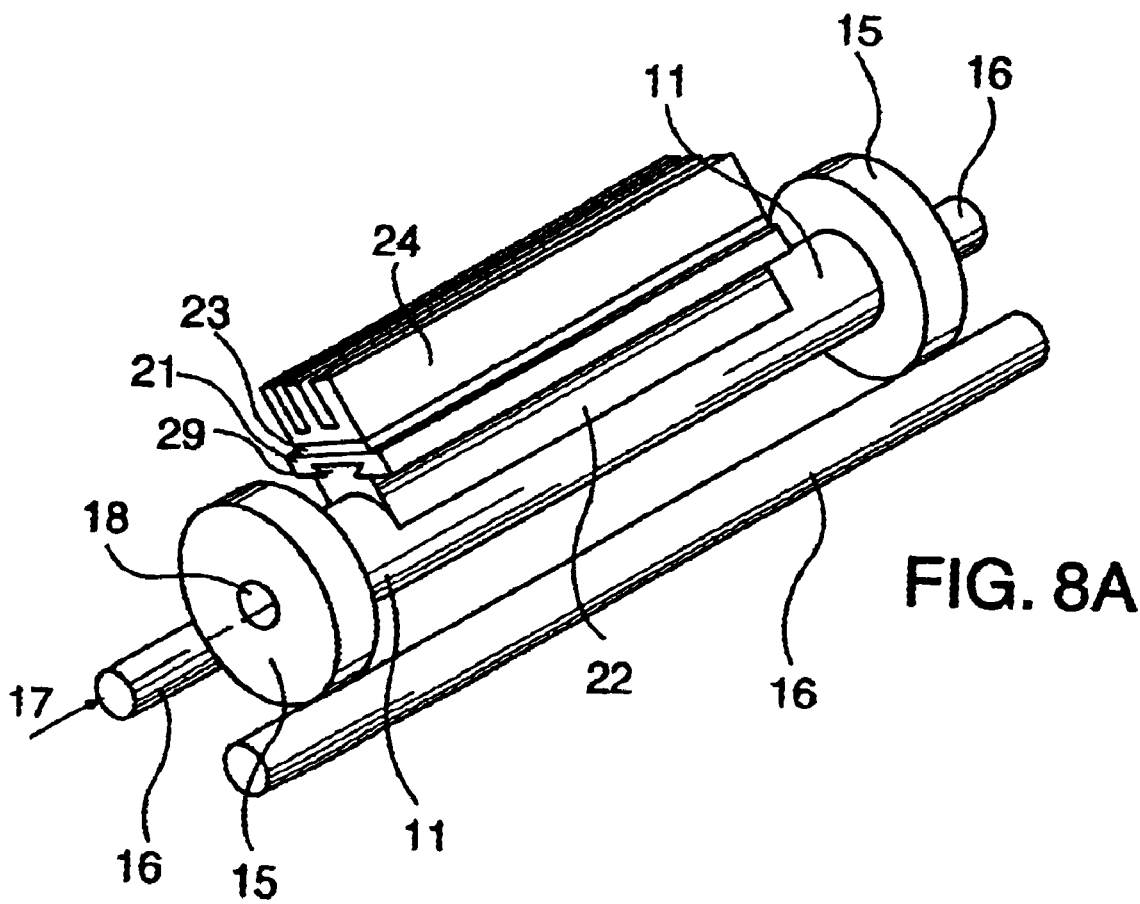
FIGS. 8(A) and 8(B) are perspective and sectional views respectively of a fifth embodiment of the cell holder according to the present invention.
Figure 8B:
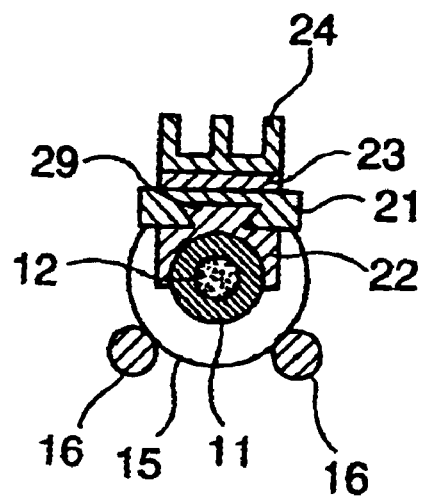

A cell holder according to a fifth embodiment of the present invention is shown in FIGS. 8(A) and 8(B). Unlike the previous embodiments shown in FIGS. 3–7, the TEC temperature control unit in this embodiment is implemented as a heat transfer element that covers on the cylindrical sample cell 11. In particular, the base plate 21 in this embodiment is not secured relative to the beam light path as in the previous embodiments, and thus has no positioning function.

The TEC temperature control unit in this embodiment comprises a heat transfer element 22 which is provided with a concave cylindrical heat transfer surface for complimentarily covering on the external surface of the cylindrical sample cell 11. The heat transfer element 22 is detachably connected with the base plate 21, e.g., by a dove-tail connection 29, so that the base plate 21 may connect with different heat transfer element 22 for different sizes of the sample cells 11. A TEC element 23 is attached to the base plate 21 for providing temperature control to sample cell 11 through the base plate 21 and the heat transfer element 22. The temperature of the TEC element 23 is controllable at a predetermined point by an electric current as well know in the art. The TEC element 23 is also provided with heat sink 24 comprising multiple cooling fins.

In this embodiment, the TEC temperature control unit may be provided as a separate device that is physically independent of the polarimeter, since it does not interfere with the positioning of the sample cell 11.

Figure 1A:
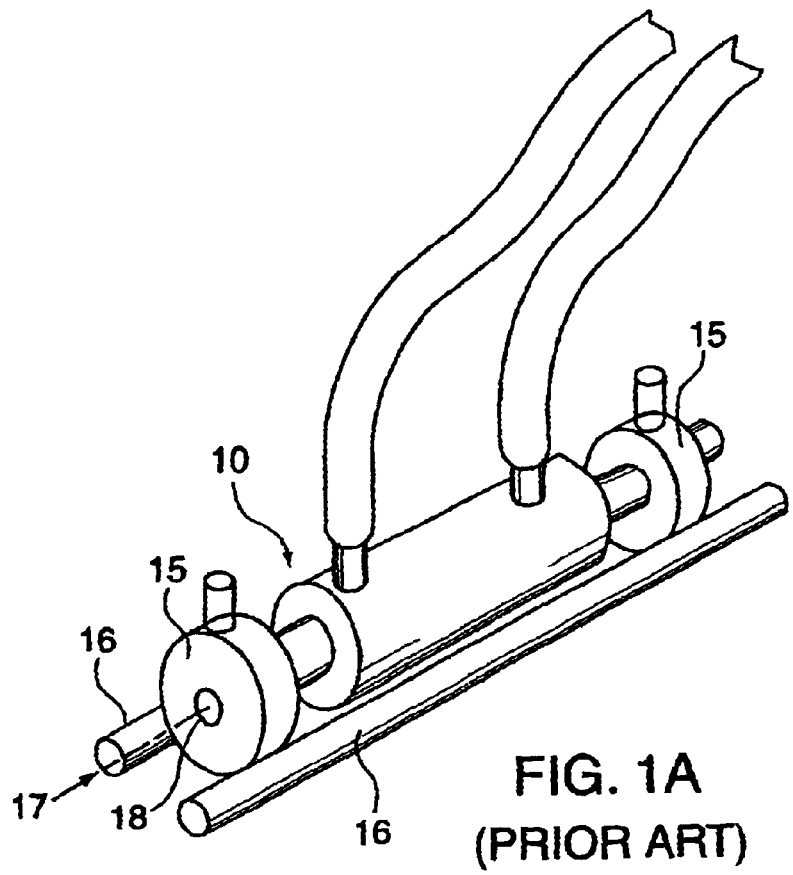
FIGS. 1(A) and 1(B) are perspective and sectional views respectively of a prior art conventional standard cylindrical sample cell and the positioning rails supporting the sample cell.
Figure 1B:
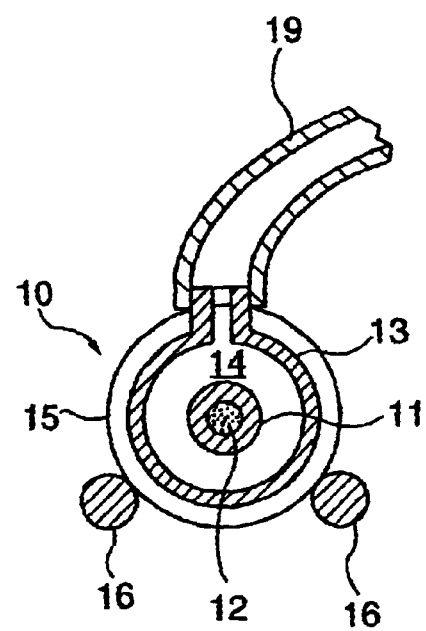
Figure 2:
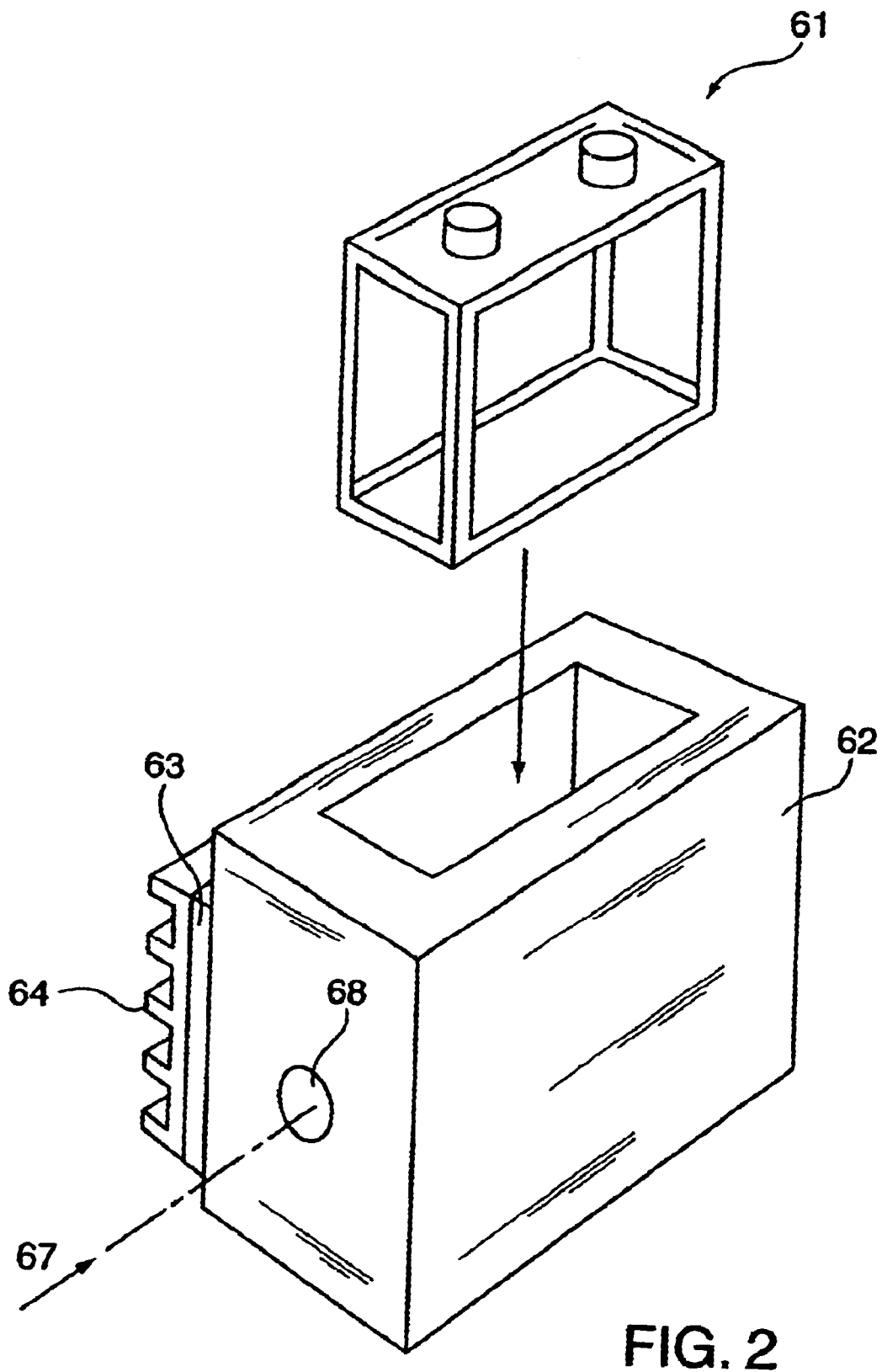
FIG. 2 is a perspective view of a prior art rectangular cell holder for holding a rectangular sample cell with a TEC element for temperature control.

The positioning of the cylindrical sample cell 11 in this embodiment is realized solely by a pair of parallel rails on which a pair of flanges 15 sit, just as in the conventional way shown in FIGS. 1(A) and 1(B). Therefore, the cell holder in this embodiment also works well with the conventional standard cylindrical sample cells. Unlike the embodiment shown in FIGS. 3(A) and 3(B), the flanges 15 here are full circular in shape and do not need to be partly removed.

Figure 9:
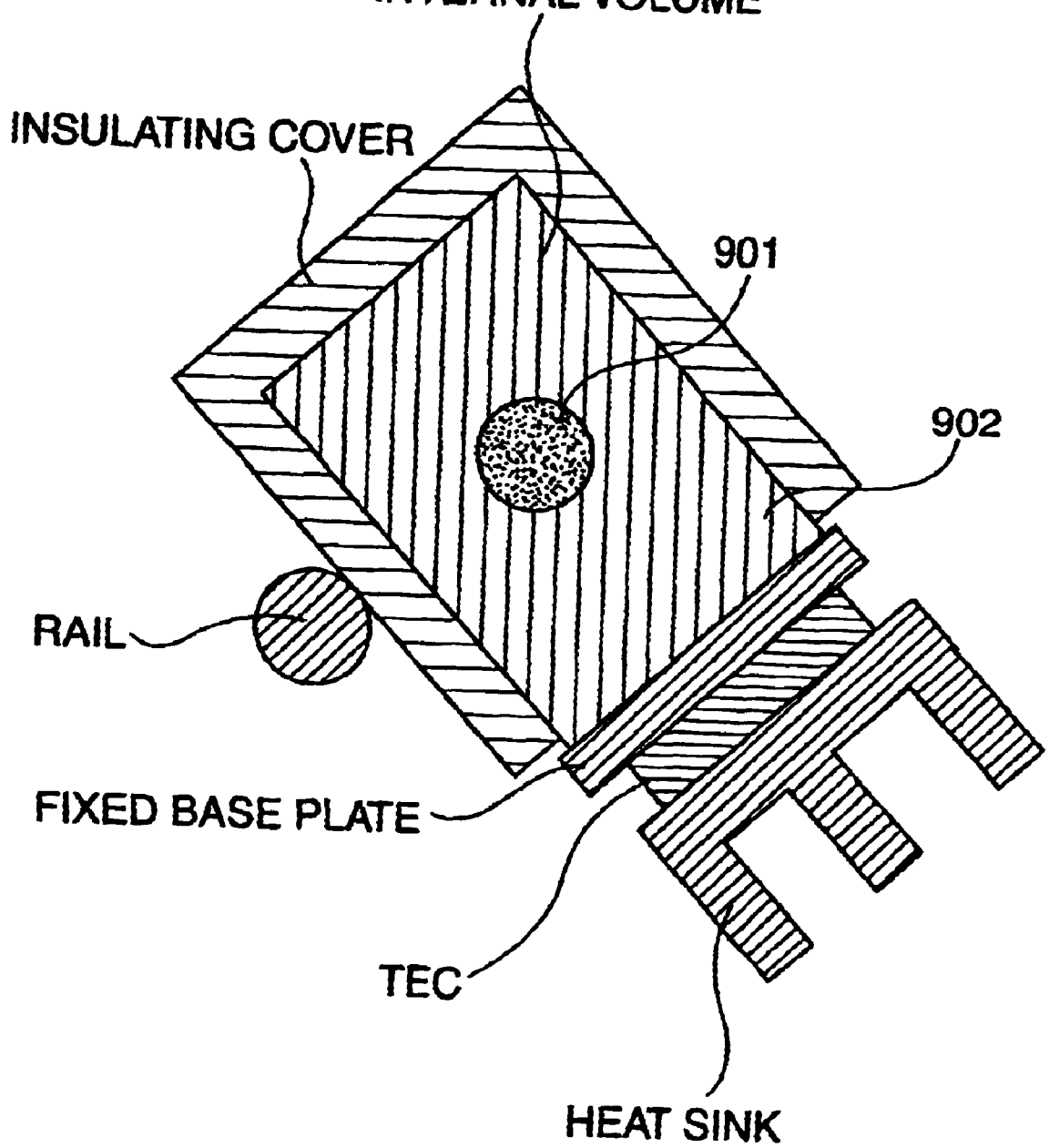
FIG. 9 shows an alternative embodiment of the invention wherein the portion of the cell holding the sample and the surrounding material are integral with each other.

FIG. 9 shows an additional embodiment of the present invention in which a cylindrical bore 901 is surrounded by material 902. The embodiment of FIG. 9 is somewhat different from the other embodiments in that the surrounding material 902 is not a separate portion that gets connected to the cell. Instead, the material 902 and bore 901 are formed from a single integral part. Notably, as used herein the concave cylindrical heat transfer surface that contacts the cell is intended to cover the junction between the material 902 and the bore 901 in the case of embodiments such as those of FIG. 9, wherein the two are made from a single part.

The above has described the preferred exemplary embodiments of the present invention. It shall be appreciated, however, that numerous alternations, modifications and changes are possible to those skilled in the art without departing the gist of the present invention. For example, in the embodiment in FIGS. 5(A) and (B), a block may be provided on the slant upper surface of the base plate 21 for the purpose of, as an alternative to the rail 16, stopping the cell mount 22 at the predetermined position. In the embodiment in FIGS. 8(A) and 8(B), the base plate 21 can be eliminated if the heat transfer element 22 is connected directly to the TEC element 23 to form an integral device for each size of the cylindrical sample cell 11. Therefore, the scope of the invention is to be solely defined by the accompanying claims.

What is claimed is:

1. A sample cell having a length for use in a polarimeter, comprising:
    a substantially flat surface of a heat conductive material for transferring heat between a heating surface and a material inside said cell, said substantially flat surface being shorter in length than said length of said sample cell and
    a positioning means for positioning said sample cell at a predetermined position such that a polarized light beam longitudinally passes through said sample cell.

2. The cell of claim 1 wherein said cell is comprised of a cell holder and an inner cell, and further comprising a thermal electric conductor temperature control means, and wherein said thermal electric conductor temperature control means comprises a thermal electric conductor element that is made of thermal electric conductor material, a temperature of which is controllable by an electric current.

3. The cell of claim 2, wherein said thermal electric conductor temperature control means further comprises a heat transfer element having a concave cylindrical heat transfer surface and being thermally conductive with said thermal electric conductor element.

4. The cell of claim 3, wherein said heat transfer element is made of a thermally conductive material.

5. The cell of claim 4, wherein said heat transfer element is thermally conductive to said thermal electric conductor element through a base plate.

6. The cell of claim 5, wherein said heat transfer element is detachably connected to said base plate.

7. The cell of claim 6, wherein said heat transfer element is detachably connected to said base plate by a dovetail connection.

8. The cell of claim 5 wherein said base plate is fixedly secured in position relative to a polarized measuring light beam that passes through said cylindrical sample cell.

9. A polarimeter, comprising:
    a substantially flat surface upon which a sample cell removably rests, and a support member upon which said sample cell also removably rests, said substantially flat surface and said support member being arranged to support said sample cell to permit light to pass through said sample cell longitudinally, said substantially flat surface home adjacent to a beam of light that passes through said sample cell longitudinally; and
    a temperature control unit being thermally conductive with said substantially flat surface.

10. The polarimeter of claim 9 wherein said temperature control unit comprises a thermo electric cooler (TEC) element with a temperature controllable by an electronic circuit.

11. The polarimeter of claim 10 wherein said substantially flat surface is a slanted surface forming a slope.

12. The polarimeter of claim 11 wherein said support member comprises a rail longitudinally parallel to said substantially flat surface.

13. The polarimeter of claim 12 wherein said rail is positioned to abut a side wall of said cell when said cell is placed in said polarimeter for preventing said cell from sliding down along said slanted surface.

14. The polarimeter of claim 12 wherein said rail is positioned to abut a pair of flanges provided at opposite ends of said sample cell while said sample cell rests on said flat surface.

15. The polarimeter of claim 13 wherein said flanges are shaped such that said flanges do not contact said substantially flat surface.

16. The polarimeter of claim 15 wherein said rail is positioned such that, when said sample cell with a pair of full-circular flanges at opposite ends rests directly on said slanted flat surface and said rail, said light beam passes through said sample cell.

17. The polarimeter of claim 16 wherein said sample cell includes a water jacket for temperature control.

18. A polarimeter for a sample element comprising:
a base plate fixedly secured in position relative to a polarized measuring light beam passing through said sample cell, said base plate having a slant flat surface; and
a horizontal rail parallel to said slant flat surface of said base plate.

19. The polarimeter of claim 18 wherein a temperature of said slanted surface is controlled by a temperature control unit.

20. The polarimeter of claim 19 wherein said temperature control unit comprises a thermal electric conductor element which temperature is controllable by electric circuitry.

21. The polarimeter of claim 20 wherein said rail is positioned such that, when said sample cell sits directly on said slanted flat surface of said base plate and said rail, said light beam passes longitudinally through said sample cell.

22. The polarimeter of claim 21 wherein said cylindrical sample cell is a conventional standard sample cell having a sample chamber containing sample substance and a water jacket around said sample chamber for temperature control.

23. The polarimeter of claim 22 wherein said conventional standard sample cell comprises a pair of full-circular flanges at opposite ends for sitting directly on said slanted flat surface of said base and said rail.

24. The polarimeter of claim 20 comprising a cell holder 43 further comprising a cell mount having a concave cylindrical surface for complimentarily accommodating a cylindrical inner sample cell.

25. The polarimeter of claim 24 wherein said cell mount is made of a thermally conductive material, and comprises a flat surface opposite to said concave cylindrical surface so as to rest on said slant flat surface of said base plate.

26. The polarimeter of claim 25 wherein said rail is positioned to abut a pair of flanges provided at opposite ends of said cell.

27. The polarimeter of claim 26 wherein said flanges are partly removed such that said flanges do not contact said flat surface of said base plate.

28. The polarimeter of claim 27 wherein said sample cell comprises a sample chamber for containing a sample substance, said sample chamber having an external cylindrical surface for complimentarily engaging with said concave cylindrical surface of said cell mount.

29. A sample cell for containing a sample substance for measurement in a polarimeter, comprising:
a cylindrical tube forming a sample chamber for containing said sample substance, wherein said tube is made of a thermally conductive material and has a substantially flat outer surface, and a light permeable opening at each end thereof.

30. The sample cell of claim 29 further comprising a pair of flanges for sealing said sample chamber at its opposite ends.

31. The sample cell of claim 30 wherein each of said flanges is in a shape of a circle with a partially removed portion.

32. A temperature control apparatus for controlling temperature of a sample cell in a polarimeter, the polarimeter having a light producing means oriented to transmit light longitudinally through said sample cell, the temperature control apparatus comprising a substantially flat plate for supporting a polarimeter cell, and a temperature control unit for controlling temperature of said substantially flat plate, the polarimeter also comprising a support member to hold a cylindrical cell.

33. The temperature control apparatus of claim 32 wherein said temperature control unit comprises a thermal electric conductor element which temperature is controllable by electric circuitry.

34. The temperature control apparatus of claim 33 further comprising a heat transfer element.

35. The temperature control apparatus of claim 34 further comprising a base plate for conducting heat between said heat transfer element and said thermal electric conductor element, said base plate being made of a thermally conductive material.

36. The temperature control apparatus of claim 35 wherein said heat transfer element is a cell mount for supporting a sample cell.

37. The temperature control apparatus of claim 36 where in said base plate is fixed secured in position relative to a polarized measuring light beam that passes through said sample cell.

38. The temperature control apparatus of claim 37 wherein said cell mount has a flat surface.

39. The temperature control apparatus of claim 38 wherein said heat transfer element is a cover placed on said cylindrical sample cell with said concave cylindrical heat transfer surface engaging with an external cylindrical surface of said sample cell, said cover being made of a thermally conductive material.

40. The temperature control apparatus of claim 39 further comprising a base plate for providing thermal conductivity between said heat transfer element and said thermal electric conductor element, said base plate being made of a thermally conductive material.

41. The temperature control apparatus of claim 40 wherein said heat transfer element is connected to said base plate through a detachable connection.

42. The temperature control apparatus of claim 41 wherein said detachable connection is a dove-tail connection.

43. The temperature control apparatus of claim 42 wherein said thermal electric conductor element further comprises a heat sink having multiple cooling fins.

44. The temperature control apparatus of claim 43 further comprising an enclosing member to form, together with said concave cylindrical surface, a longitudinally complete enclosure around said sample cell for keeping said sample cell apart from ambient temperature.

45. The temperature control apparatus of claim 44 wherein said enclosing member is made of a thermally insulative material.

46. The temperature control apparatus of claim 45 wherein said enclosing member is made of a thermally conductive material.

47. A polarimeter for measuring optical activities of a sample substance, comprising:

a sample cell for accommodating said sample substance to be measured, said sample cell being made of a thermally conductive material and having a positioning means on an outer surface thereof for positioning said sample cell in a predetermined position such that a polarized measurement light beam passes longitudinally through said sample cell; and a temperature control unit having a substantially planar heat transfer surface for contacting a substantially planar external surface of said sample cell so as to keep said sample cell at a predetermined temperature, and an additional nonplanar surface to aid in positioning said sample cell.

48. The polarimeter of claim 47 wherein said temperature control unit comprises a thermal electric conductor element.

49. A method of performing polarimetry comprising the steps of placing a cell with a substantially planer surface and a substantially non planar surface on a second substantially planar surface and a support member, allowing said cell to rest freely on said second substantially planar surface and said support member, and shining a polarized light beam longitudinally through said cell.

50. The method of claim 49 further comprising heating or cooling at least one of said support member or said second substantially planar surface.

51. The method of claim 49 further comprising removing said cell from said second substantially planar surface and said support member by simply lifting said cell away from said second substantially planar surface without having to move either said substantially planar surface or said support member.

52. The method of claim 51 wherein said substantially planar surface is supported by said second substantially planar surface and wherein said support member supports two flanges on ends of said cell.

53. A polarimeter including a substantially flat member and a support member for cooperatively supporting polarimeter cells, said substantially flat member and said support member being oriented to support cells that have a flat outer surface, and to interchangeably align either type of said cells with a longitudinal beam.

54. The polarimeter of claim 53 wherein said support member is nonplanar.

55. The polarimeter of claim 53 wherein said support member is a rail.

* * * * *